(12) United States Patent
Akahane et al.

(10) Patent No.: US 12,027,814 B2
(45) Date of Patent: Jul. 2, 2024

(54) LASER DEVICE, LIGHT SOURCE, AND MEASUREMENT APPARATUS, AND METHOD FOR USING A LASER DEVICE

(71) Applicant: National Institutes for Quantum Science and Technology, Chiba (JP)

(72) Inventors: Yutaka Akahane, Kizugawa (JP); Makoto Aoyama, Kizugawa (JP); Kanade Ogawa, Kizugawa (JP); Koichi Yamakawa, Kizugawa (JP)

(73) Assignee: National Institutes for Quantum Science and Technology, Chiba (JP)

( * ) Notice: Subject to any disclaimer, the term of this patent is extended or adjusted under 35 U.S.C. 154(b) by 0 days.

(21) Appl. No.: 17/823,569

(22) Filed: Aug. 31, 2022

(65) Prior Publication Data

US 2022/0416499 A1    Dec. 29, 2022

Related U.S. Application Data

(63) Continuation of application No. 16/641,803, filed as application No. PCT/JP2018/031387 on Aug. 24, 2018, now Pat. No. 11,482,831.

(30) Foreign Application Priority Data

Sep. 5, 2017    (JP) ................. 2017-170416

(51) Int. Cl.
*H01S 3/094*    (2006.01)
*H01S 3/04*    (2006.01)
(Continued)

(52) U.S. Cl.
CPC ............ *H01S 5/005* (2013.01); *H01S 3/0401* (2013.01); *H01S 3/0405* (2013.01);
(Continued)

(58) Field of Classification Search
None
See application file for complete search history.

(56) References Cited

U.S. PATENT DOCUMENTS 3,582,815 A * 6/1971 Siebert ................ H01S 3/08059
372/98
3,777,280 A * 12/1973 Pohl ........................ H01S 3/113
372/101
(Continued)

FOREIGN PATENT DOCUMENTS

CN          1645691 A       7/2005
CN        101320880 A      12/2008
(Continued)

OTHER PUBLICATIONS

Singh et al., "Effect of Intracavity Spatial Filtering on the Beam Characteristics of a Copper Vapor Laser", 1991, Journal of Applied Physics, 69, 537-538. (Year: 1991).*
(Continued)

*Primary Examiner* — Joshua King
(74) *Attorney, Agent, or Firm* — NK Patent Law

(57) ABSTRACT

Provided is a laser device in which: a laser medium doped with ytterbium emits light upon absorption of excitation light; the light emitted by the laser medium is amplified to obtain output light; and the output light is outputted in the form of a plurality of pulses. In the laser device, a spatial filter is disposed in the optical path of the light emitted by the laser medium or is disposed in the optical path of the output light outputted from an optical resonator, the spatial filter being configured to filter out a portion of the light or of the output light around the optical axis.

16 Claims, 8 Drawing Sheets

US 12,027,814 B2
Page 2

(51) Int. Cl.
| | |
|---|---|
| *H01S 3/042* | (2006.01) |
| *H01S 3/06* | (2006.01) |
| *H01S 3/08045* | (2023.01) |
| *H01S 3/0805* | (2023.01) |
| *H01S 3/0941* | (2006.01) |
| *H01S 3/113* | (2006.01) |
| *H01S 3/16* | (2006.01) |
| *H01S 5/00* | (2006.01) |
| *H01S 3/00* | (2006.01) |

(52) U.S. Cl.
CPC ...... *H01S 3/0627* (2013.01); *H01S 3/094076* (2013.01); *H01S 3/09415* (2013.01); *H01S 3/113* (2013.01); *H01S 3/1618* (2013.01); *H01S 3/1643* (2013.01); *H01S 3/0057* (2013.01); *H01S 3/0092* (2013.01); *H01S 3/042* (2013.01); *H01S 3/08045* (2013.01); *H01S 3/0805* (2013.01)

(56) References Cited

U.S. PATENT DOCUMENTS

| | | | | |
|---|---|---|---|---|
| 5,454,004 | A * | 9/1995 | Leger | G02B 27/0037 372/99 |
| 5,627,847 | A * | 5/1997 | Leger | G02B 5/1871 372/99 |
| 6,373,864 | B1 | 4/2002 | Georges et al. | |
| 6,556,614 | B2 * | 4/2003 | Nettleton | H01S 3/1083 372/54 |
| 7,548,571 | B2 | 6/2009 | Mirov et al. | |
| 8,582,613 | B1 * | 11/2013 | Kim | H01S 3/1675 372/18 |
| 2002/0181513 | A1 * | 12/2002 | Laurell | H01S 3/0627 372/11 |
| 2003/0039274 | A1 * | 2/2003 | Neev | H01S 3/0627 372/10 |
| 2003/0063630 | A1 * | 4/2003 | Sakai | H01S 3/113 372/10 |
| 2003/0138005 | A1 * | 7/2003 | Kan | H01S 3/113 372/69 |
| 2004/0190564 | A1 | 9/2004 | Zhou | |
| 2005/0074041 | A1 * | 4/2005 | Sommerer | H01S 3/042 372/36 |
| 2005/0163186 | A1 * | 7/2005 | Petersen | H01S 5/20 372/19 |
| 2005/0281301 | A1 * | 12/2005 | Mirror | H01S 3/094046 372/41 |
| 2006/0092992 | A1 * | 5/2006 | Nettleton | H01S 3/1083 372/21 |
| 2006/0176913 | A1 * | 8/2006 | Souhaite | H01S 3/113 372/20 |
| 2008/0247425 | A1 * | 10/2008 | Welford | H01S 3/113 372/10 |
| 2008/0317072 | A1 * | 12/2008 | Essaian | H01S 3/109 372/10 |
| 2010/0018487 | A1 * | 1/2010 | Herden | F02P 23/04 123/143 B |
| 2011/0280264 | A1 * | 11/2011 | Yamazoe | H01S 3/08045 372/19 |
| 2012/0140782 | A1 | 6/2012 | Sotelo et al. | |
| 2012/0224599 | A1 * | 9/2012 | Mirov | H01S 3/08086 372/49.01 |
| 2014/0010247 | A1 * | 1/2014 | Taira | H01S 3/1115 372/11 |
| 2014/0086268 | A1 * | 3/2014 | Stultz | H01S 3/113 372/10 |
| 2014/0269786 | A1 * | 9/2014 | Roy | H01S 3/0085 372/3 |
| 2015/0010028 | A1 * | 1/2015 | Taira | H01S 3/109 372/22 |
| 2015/0077853 | A1 * | 3/2015 | Wan | H01S 3/0627 359/566 |
| 2015/0117475 | A1 * | 4/2015 | Taira | H01S 3/11 372/10 |
| 2015/0117476 | A1 * | 4/2015 | Akino | H01S 3/113 372/11 |
| 2016/0276801 | A1 * | 9/2016 | Spiekermann | H01S 3/10084 |
| 2017/0046856 | A1 | 2/2017 | Hirai et al. | |
| 2017/0201061 | A1 * | 7/2017 | Taira | H01S 3/113 |
| 2018/0000386 | A1 | 1/2018 | Yamakawa | |
| 2018/0069368 | A1 * | 3/2018 | Taira | H01S 3/08018 |
| 2018/0123309 | A1 * | 5/2018 | Taira | H01S 3/0627 |
| 2018/0309261 | A1 * | 10/2018 | Taira | H01S 3/1022 |

FOREIGN PATENT DOCUMENTS

| | | | | |
|---|---|---|---|---|
| CN | 103022860 | A | | 4/2013 |
| CN | 106422088 | A | | 2/2017 |
| DE | 69731475 | T2 | | 10/2005 |
| DE | 69731475 | T2 * | 10/2005 | ........... H01S 3/0627 |
| DE | 102013101760 | A1 | | 5/2014 |
| DE | 102013101760 | A1 * | 5/2014 | ......... B23K 26/0096 |
| DE | 102015005257 | A1 | | 10/2016 |
| DE | 102015005257 | A1 * | 10/2016 | |
| GB | 2539046 | A | | 12/2016 |
| GB | 2539046 | A * | 12/2016 | ............... H01S 3/11 |
| JP | H09127567 | A * | 5/1997 | |
| JP | 2005136291 | A | | 5/2005 |
| JP | 2014003262 | A * | 1/2014 | ........... H01S 3/1675 |
| JP | 2014003262 | A | | 1/2014 |
| JP | 2017123429 | A | | 7/2017 |
| WO | 9303522 | A1 | | 2/1993 |
| WO | WO-9303522 | A1 * | 2/1993 | ........... H01S 3/1112 |
| WO | 2004027945 | A1 | | 4/2004 |
| WO | WO-2004027945 | A1 * | 4/2004 | ......... H01S 3/08045 |
| WO | 2007064298 | A1 | | 6/2007 |
| WO | WO-2007064298 | A1 * | 6/2007 | ......... H01S 3/09415 |
| WO | 2009030550 | A1 | | 3/2009 |
| WO | WO-2009030550 | A1 * | 3/2009 | ............. F02P 23/04 |
| WO | 2016117520 | A1 | | 7/2016 |

OTHER PUBLICATIONS

ISA/JP, International Search Report for corresponding PCT Patent Application No. PCT/JP2018/031387, mailed Nov. 13, 2018, 2 pages.
WIPO, International Preliminary Report on Patentability for corresponding PCT Patent Application No. PCT/JP2018/031387, issued Mar. 10, 2020, 5 pages.
Taira Takunori et al.: "Promise of Giant Pulse Micro-Laser for Engine Ignition", J. Plasma Fusion Research, vol. 89, No. 4, pp. 238-241 (2013), 5 pages total.
Hiroshi Sakai et al.: ">1MW Peak Power Single-Mode High-Brightness Passively Q-Switched Nd3+: YAG Microchip Laser", Optics Express, vol. 16, No. 24, pp. 19891-19899, Nov. 24, 2008, 9 pages total.
EPO, Extended European Search Report for corresponding European Patent Application No. 18854859.8 mailed May 14, 2021, 9 pages.
USPTO; Non-Final Action for U.S. Appl. No. 16/641,803 dated Oct. 22, 2021, 13 pages.
USPTO; Notice of Allowance for U.S. Appl. No. 16/641,803 dated Jun. 29, 2022, 12 pages.
CNIPA, First Office Action for corresponding Chinese Patent Application No. 201880057399.3, mailed Feb. 22, 2021, 10 pages.
Walter Koechner: "Solid-State Laser Engineering", published on May 2002, pp. 190-192, p. 201.

* cited by examiner (a)

(b)

LASER DEVICE, LIGHT SOURCE, AND MEASUREMENT APPARATUS, AND METHOD FOR USING A LASER DEVICE

CROSS-REFERENCE TO RELATED APPLICATIONS

This application is a continuation of a U.S. application Ser. No. 16/641,803 filed on Feb. 25, 2020, which was the U.S. National Stage of International Patent Application No. PCT/JP2018/031387, filed on Aug. 24, 2018, which claims priority to Japanese Patent Application No. 2017-170416, filed on Sep. 5, 2017, the entire content of all of which is incorporated by reference herein.

TECHNICAL FIELD

The present invention relates to a configuration of a laser device that generates pulsed laser light by passive Q-switching, and relates to a method of driving the laser device.

BACKGROUND ART

Oscillation of laser light is caused by introducing excitation light into an optical resonator that is configured such that a laser medium is disposed in the optical path between an incident mirror and an exit mirror. One technique to generate pulsed laser light is Q-switching. Q-switching is a technique to control oscillation by a Q-switch provided inside the optical resonator, and is roughly categorized into active Q-switching and passive Q-switching. In cases of active Q-switching, a Pockels cell or the like serving as the Q-switch needs to be externally controlled actively in order to cause laser light to oscillate. On the other hand, in cases of passive Q-switching, a saturable absorber is used instead of a Pockels cell or the like, and light absorption and light transmission in the saturable absorber are automatically controlled, so that the saturable absorber serves as the Q-switch. As such, passive Q-switching eliminates the need for active control, and thus makes it possible to simplify the device structure, reduce the size of the device, and offer the device for a reasonable price. Thus, resonators which employ passive Q-switching are particularly preferably used in small-size laser devices.

Widely-used small-size laser oscillators (laser devices) employing passive Q-switching are those which include Nd:YAG as a laser medium. In cases where Nd:YAG is used, oscillation wavelength is 1064 nm and laser light emitted by a laser diode can be used as excitation light, and thus the laser device as a whole can be reduced in size easily. In such cases, the times of occurrence of pulses of output laser light can be controlled by controlling the times of occurrence of pulses of excitation light. Such a small-size laser device has been developed mainly for the purpose of igniting an engine of an automobile and the like. In cases where laser light is used to ignite an engine, the laser light preferably has high peak intensity and short pulse width (output pulse width), because such laser light achieves good energy efficiency in engine ignition. A passively Q-switched laser including Nd:YAG as a laser medium is capable of easily generating short pulses on the order of a picosecond ($10^{-12}$ second), which is shorter than a pulse width of 1 ns (nanosecond: $10^{-9}$ second), and thus is capable of providing particularly preferred characteristics when used as a laser for engine ignition. Non-patent Literature 1 discloses an arrangement in which Yb:YAG is used as a laser medium and a laser diode is used as a source of excitation light and thereby laser light with such short pulse widths (output pulse width) is generated. Furthermore, relationships between the output pulse width of light generated using passively Q-switched laser and various parameters are disclosed in, for example, Non-patent Literature 2. As such, conventionally, many passively Q-switched lasers have employed Nd:YAG as a laser medium, which easily achieves high output.

On the other hand, also for purposes other than engine ignition, use of such a small-size laser device makes it possible to reduce the size of an apparatus as a whole. For example, in a blood glucose meter like that disclosed in Patent Literature 1, infrared light (laser light) directly used in measurement is obtained by optical parametric oscillation (OPO). In OPO, by introducing pump light into a non-linear crystal, light having a different wavelength from the pump light is caused to oscillate, and the light obtained through the oscillation is directly used in measurement of blood glucose level. The pump light used here is mid-infrared laser light, and therefore the aforementioned small-size laser device employing passive Q-switching is preferred also in order to generate pump light in such a blood glucose meter.

CITATION LIST

Patent Literature

Patent Literature 1

PCT International Publication No. WO 2016/117520

Non-Patent Literatures

Non-Patent Literature 1

"Promise of Giant Pulse Micro-Laser for Engine Ignition", TAIRA Takunori, TSUNEKANE Masaki, KANEHARA Kenji, MORISHIMA Shingo, TAGUCHI Nobuyuki, SUGIURA Akimitsu, Journal of plasma and fusion research 89(4) p. 238 (2013)

Non-Patent Literature 2

">1 MW Peak Power Single-Mode High-Brightness Passively Q-Switched Nd3+:YAG Microchip Laser", H. Sakai, H. Kan, and T. Taira, Optics Express, vol. 16, p. 19891 (2008)

SUMMARY OF INVENTION

Technical Problem

When the foregoing small-size laser device employing passive Q-switching is used, different pulse widths are necessary for the case of the foregoing engine ignition and for the case of a blood glucose meter (pump light for OPO). In particular, in cases where mid-infrared light with a wavelength not less than 3 μm is to be caused to oscillate in OPO, the gain is small because of a small optical constant of the non-linear crystal used in OPO, and also the non-linear crystal is damaged by irradiation energy of 10 $MW/cm^2$ or greater. Therefore, in such cases, pump light with a relatively low intensity and a long pulse of not less than 4 ns is used. For example, it is most preferable that the length of the non-linear crystal in the direction of the optical axis of incident/output light is, for example, about 20 mm, and that the pulse width of pump light is, for example, about 10 ns. This pulse width is significantly longer than the pulse width for the case of engine ignition disclosed in Non-Patent Literature 1. That is, the pump light for OPO is required to have a longer output pulse width than that for the cases disclosed in Non-patent Literature 1 and the like.

Non-patent Literature 2 discloses that the output pulse width $t_p$ of light generated using passively Q-switched laser and cavity length $l_c$ (optical length between the incident mirror and the exit mirror in consideration of refractive index) are in linear relation to each other. Specifically, Non-patent Literature 2 discloses that the output pulse width $t_p$ is represented by the following equations (1) to (4):

$$t_p = \frac{p \cdot \ln \delta_f}{c \cdot \ln T_0} l_c \cdot \left[ 1 - \delta_t - \frac{\beta p}{\alpha}(1 - \delta_t^\alpha) + (1 - \beta p) \cdot \ln \delta_t \right]^{-1} \quad (1)$$

$$p = \frac{-2\ln T_0}{-\ln R + L_g - 2\ln T_0} \quad (2)$$

$$\alpha = a \cdot \frac{\sigma_{SA} A_{SA}}{\sigma_g A_g} \quad (3)$$

$$\beta = \frac{\sigma_{SA} - \sigma_{ESA}}{\sigma_{SA}} \quad (4)$$

where: c is the speed of light, $T_0$ is the initial transmittance of the saturable absorber, $\delta_f$ is the ratio between the final and initial population inversion densities in Q-switching, and $\delta_t$ is the ratio of population inversion density when the photon number is maximum in Q-switching; and R is the reflectivity of the exit mirror of the resonator, $L_g$ is the percentage of round-trip optical loss at the resonator, $\sigma_{SA}$ and $\sigma_g$ represent the stimulated-emission cross-sections of the saturable absorber and the laser medium, respectively, $A_{SA}$ and $A_g$ represent effective areas during laser oscillation of the saturable absorber and the laser medium, respectively, $\sigma_{ESA}$ is the excited absorption cross section of the saturable absorber, and a is a constant near 1. It is apparent from the equation (1) that, in order to increase the output pulse width $t_p$, it is only necessary to increase the cavity length $l_c$. That is, a passively Q-switched laser in which the cavity length $l_c$ has a large value can be used as a source of pump light for OPO.

However, the output pulse width $t_p$ depends not only on the cavity length $l_c$ but also on other parameters. Note here that the stimulated-emission cross-section $\sigma_g$ of the laser medium differs greatly depending on the type of laser medium. In cases where Nd:YAG, which is widely used as the laser medium as described earlier, is used, the stimulated-emission cross-section $\sigma_g$ is large; therefore, in order to obtain a large pulse output through Q-switching, it is necessary to have oscillation strongly limited by the saturable absorber, and thus necessary to reduce the initial transmittance $T_0$ of the saturable absorber (equal to or less than 0.3). This works such that the output pulse width $t_p$ becomes shorter, and therefore is advantageous for generation of picosecond short pulses for use in engine ignition as described earlier. However, this is disadvantageous when used as the foregoing pump light for OPO.

Another known material that can be used as a laser medium in a passively Q-switched laser device similarly to Nd:YAG is Yb:YAG, which is doped with Yb instead of Nd. In cases of Yb:YAG, the oscillation wavelength is 1030 nm, and laser light emitted by a laser diode can be used as excitation light as with the case of Nd:YAG. Therefore, it is possible to obtain a small-size laser device by using Yb:YAG, as with the case of Nd:YAG. Furthermore, since the stimulated-emission cross-section $\sigma_g$ is small when Yb:YAG is used as the laser medium, it is possible to employ a large initial transmittance $T_0$ (equal to or less than 0.7). As such, the output pulse width $t_p$ can be made longer more easily than when Nd:YAG is used as the laser medium. FIG. 12 shows the dependence of the output pulse width $t_p$ on the cavity length $l_c$ in such a configuration, calculated using the equations (1) to (4).

The inventors conducted diligent studies, and found that, in order to configure a small-size passively Q-switched laser device whose laser medium contains Yb such that the output pulse width is long, it is preferable to bring a transverse oscillation mode close to single mode. The present invention was made in view of this object.

Solution to Problem

A laser device in accordance with the present invention is a laser device including an optical resonator that includes a saturable absorber and a laser medium that is arranged to emit light upon absorption of excitation light, the laser medium being arranged to emit the light upon an input of the excitation light, which is pulsed light, into the optical resonator, the optical resonator being arranged to amplify the light emitted by the laser medium to obtain laser light and output the laser light as output light, the laser medium being doped with ytterbium (Yb), a pulse width of the excitation light, a cavity length of the optical resonator, and the saturable absorber being set such that the excitation light is single-pulsed light and that the output light is composed of a plurality of pulses, the laser device comprising a spatial filter that is disposed in an optical path of the light inside the optical resonator or that is disposed in an optical path of the output light outside the optical resonator, the spatial filter being configured to filter out a portion of the light or of the output light around an optical axis.

Advantageous Effects of Invention

The present invention is arranged as described above, and therefore makes it possible, when generating high-energy nanosecond pulses in a small-sized passively Q-switched laser, to configure the laser such that the output pulse is long, and makes it possible to bring a transverse oscillation mode close to single mode.

Figure 2:
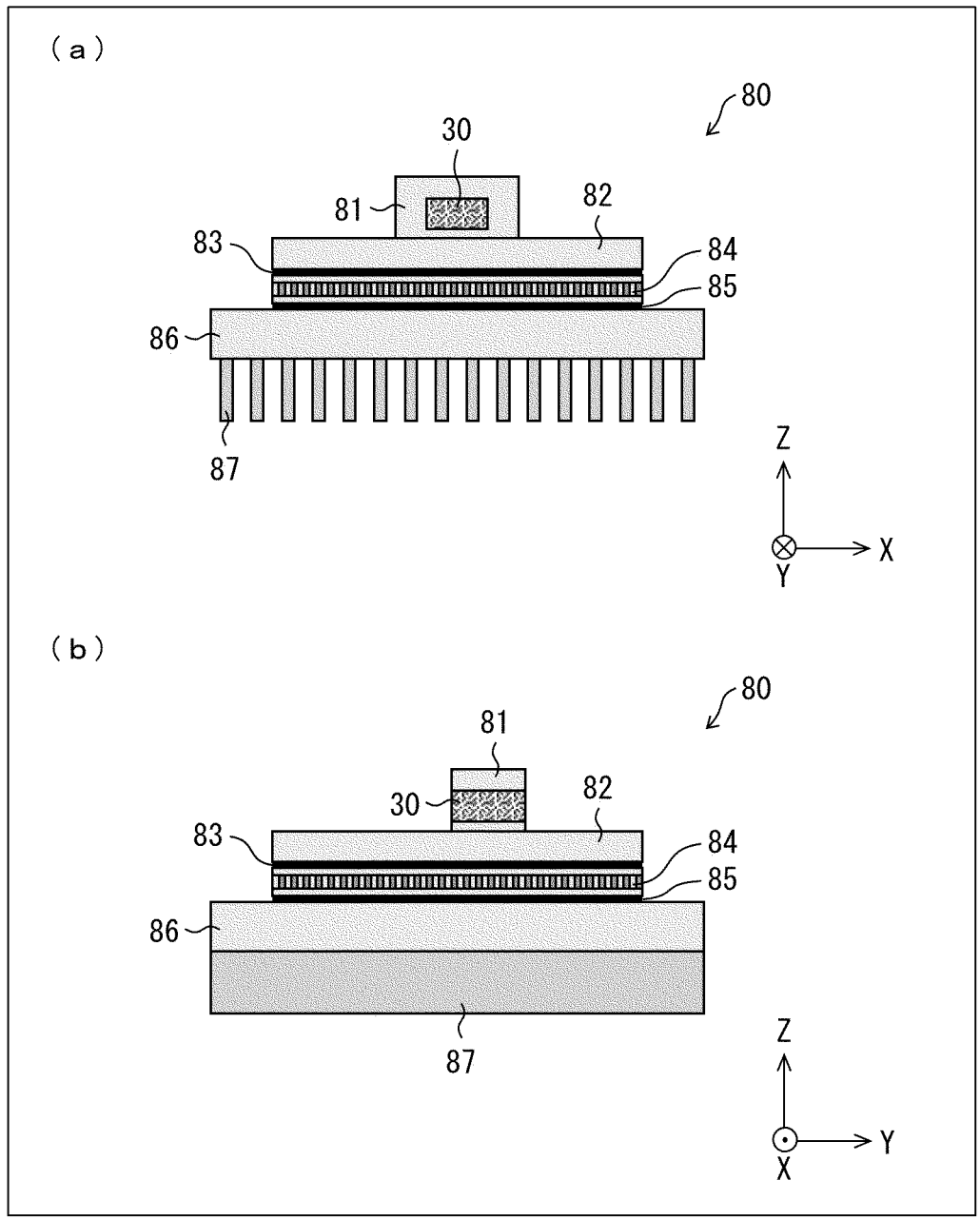

(a) of FIG. 2 is a front view of a laser medium cooler in accordance with an embodiment of the present invention, and (b) of FIG. 2 is a lateral cross-sectional view of the laser medium cooler.

Figure 3:
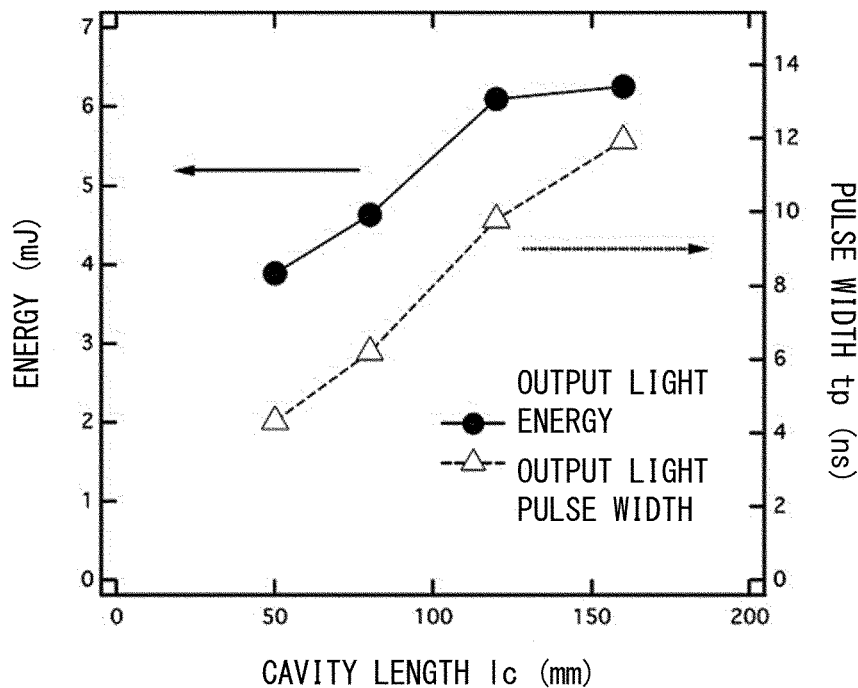

FIG. 3 shows the results of actual measurement of a relationship among the cavity length $l_c$, the pulse width $t_p$ of output light, and pulse energy in a laser device in accordance with an embodiment of the present invention.

Figure 4:
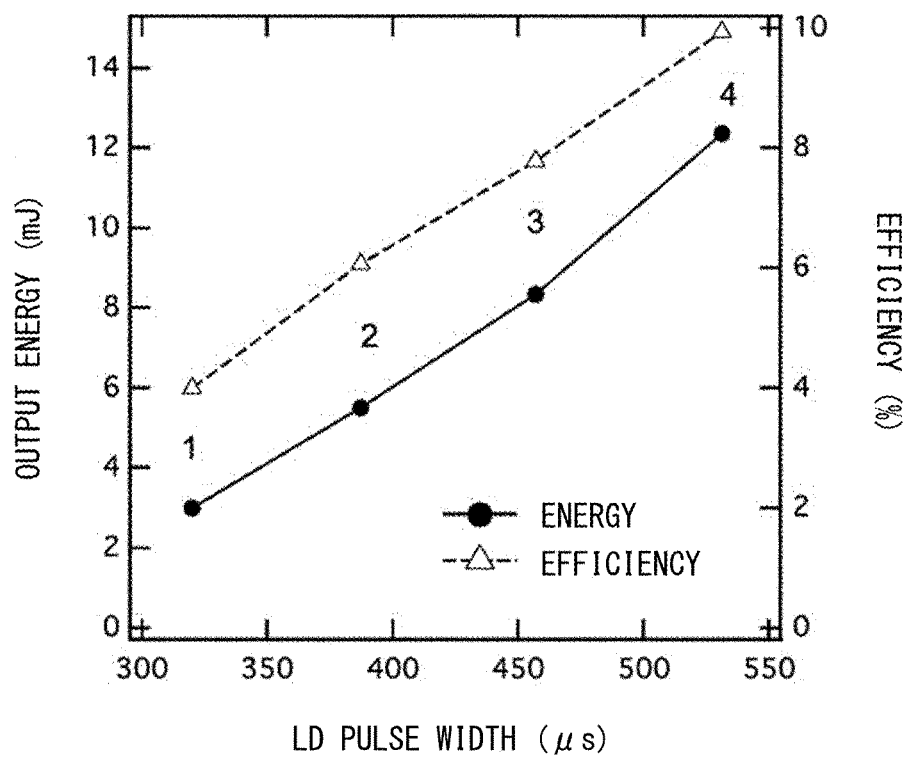

FIG. 4 shows the results of actual measurement of pulse energy of output light, which is outputted a plurality of times when excitation light is inputted once, and efficiency, in a laser device in accordance with an embodiment of the present invention.

Figure 5:
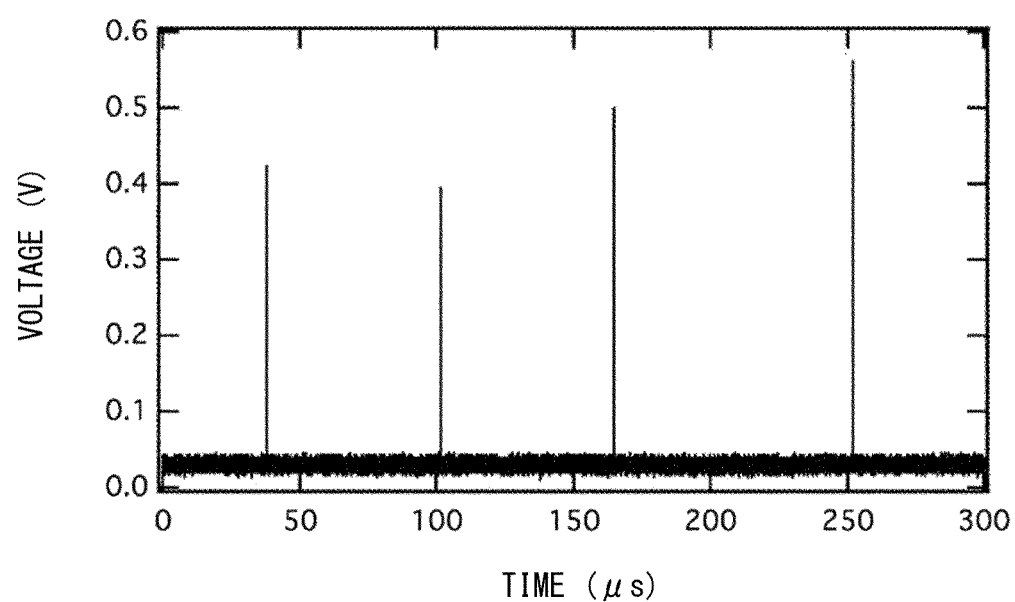

FIG. 5 shows the results of actual measurement of a situation in which output light is outputted in a pulsed form repeatedly per incidence of excitation light in a laser device in accordance with an embodiment of the present invention.

Figure 6:
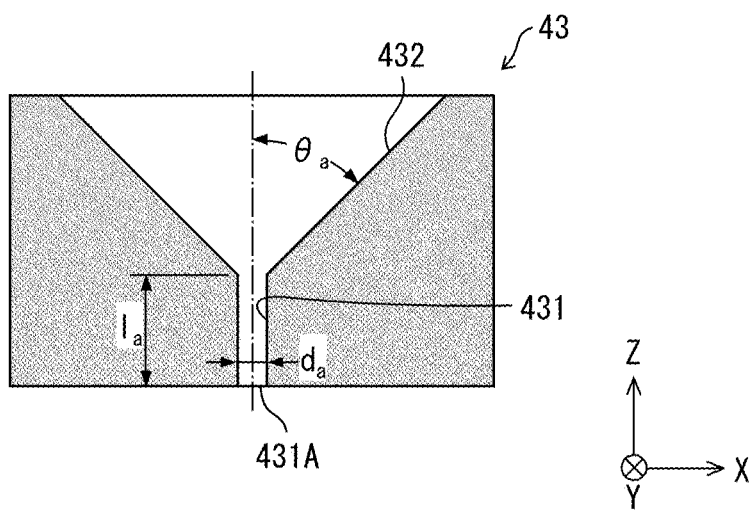
Figure 6:
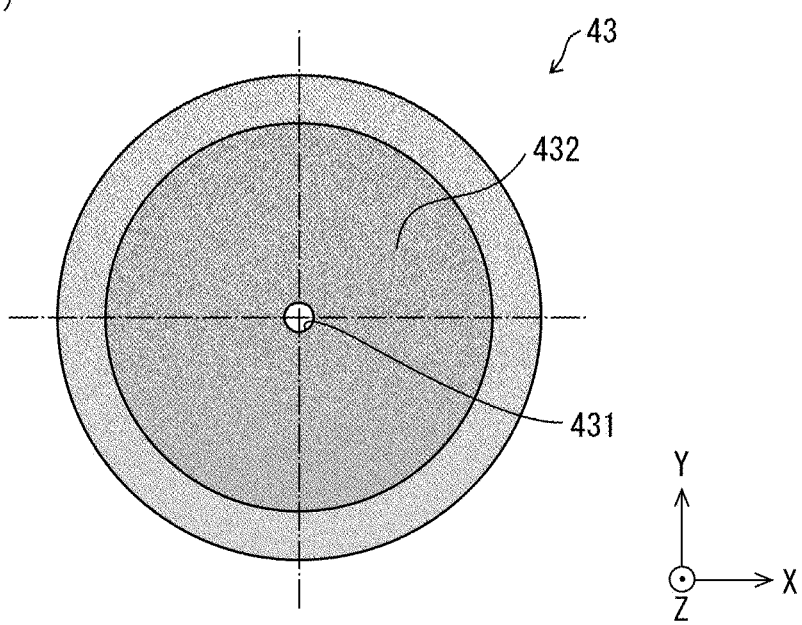

(a) of FIG. 6 is a cross-sectional view of a diaphragm in accordance with an embodiment of the present invention, and (b) of FIG. 6 is a front view of the diaphragm.

Figure 7:
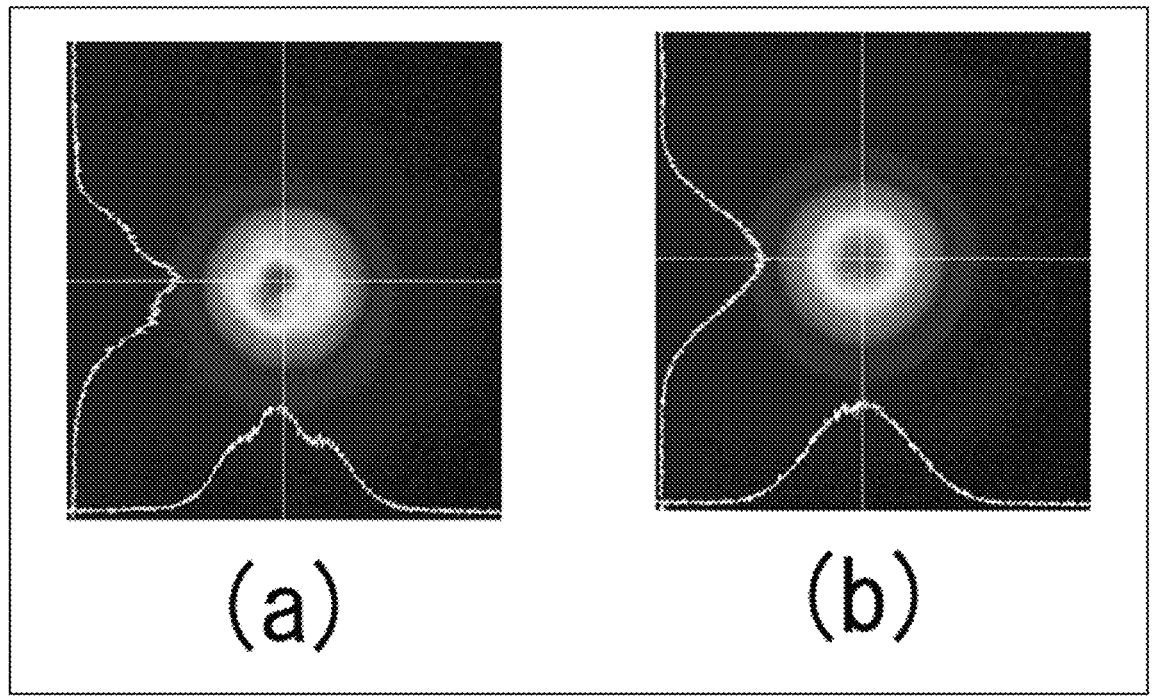

FIG. 7 shows beam profiles of output light in (a) a case where a spatial filter was not used and (b) a case where the spatial filter was used.

Figure 8:
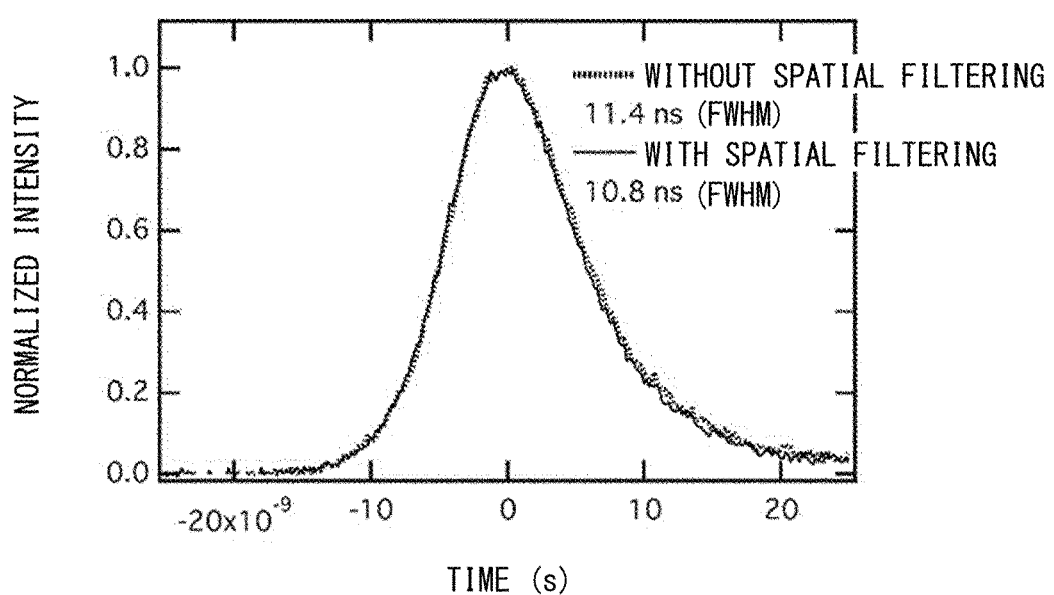

FIG. 8 shows temporal waveform of output light pulses in (a) a case where a spatial filter was not used and (b) a case where the spatial filter was used.

Figure 9:
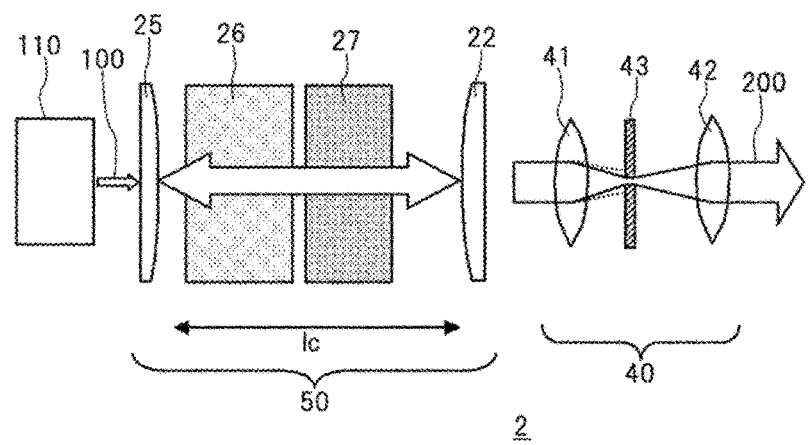

FIG. 9 illustrates a configuration of Variation 1 of a laser device in accordance with an embodiment of the present invention.

Figure 10:
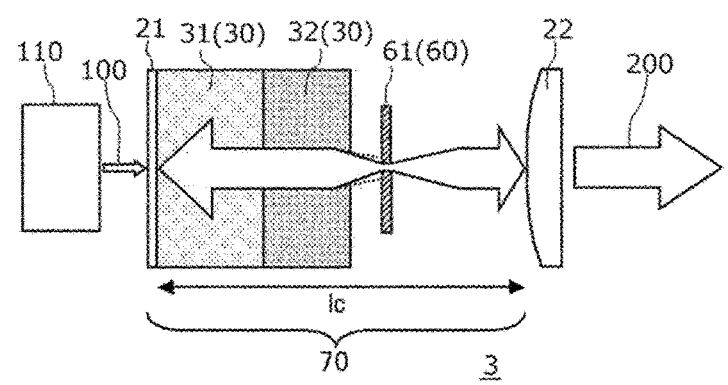

FIG. 10 illustrates a configuration of Variation 2 of a laser device in accordance with an embodiment of the present invention.

Figure 11:
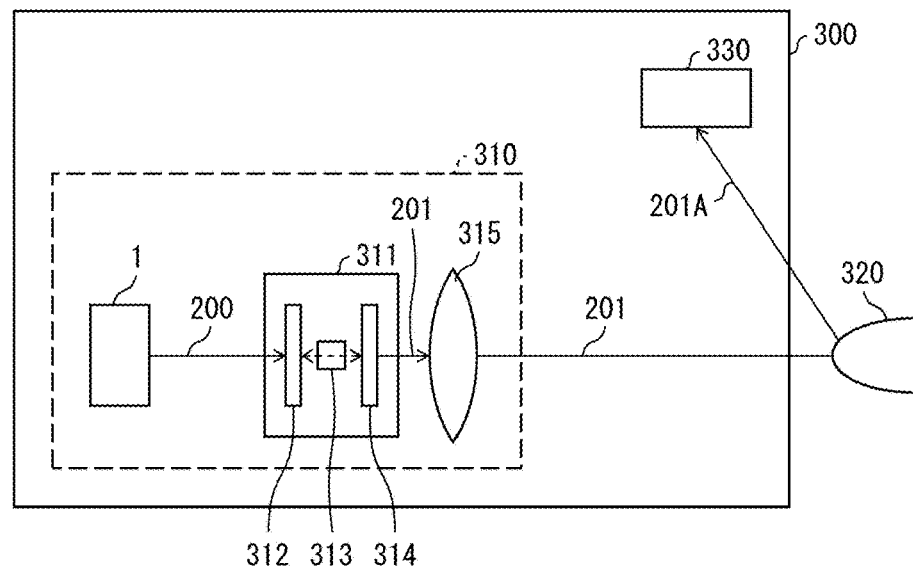

FIG. 11 illustrates a configuration of a measurement apparatus in accordance with an embodiment of the present invention.

Figure 12:
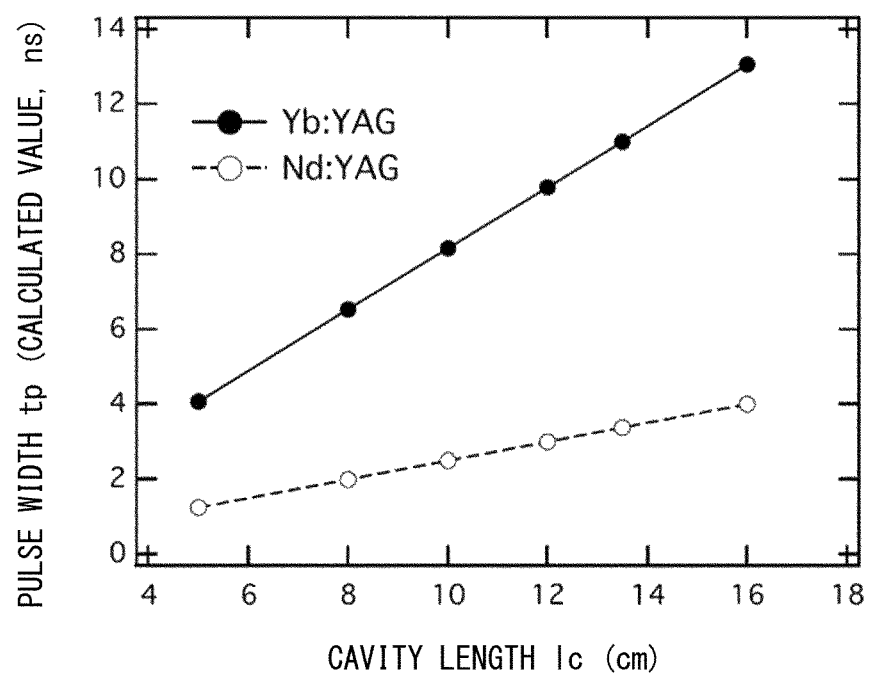

FIG. 12 shows the results of calculation of the relationship between the cavity length and the output pulse width in a case where Nd:YAG was used as a laser medium and in a case where Yb:YAG was used as the later medium.

DESCRIPTION OF EMBODIMENTS

Embodiment 1

Figure 1:
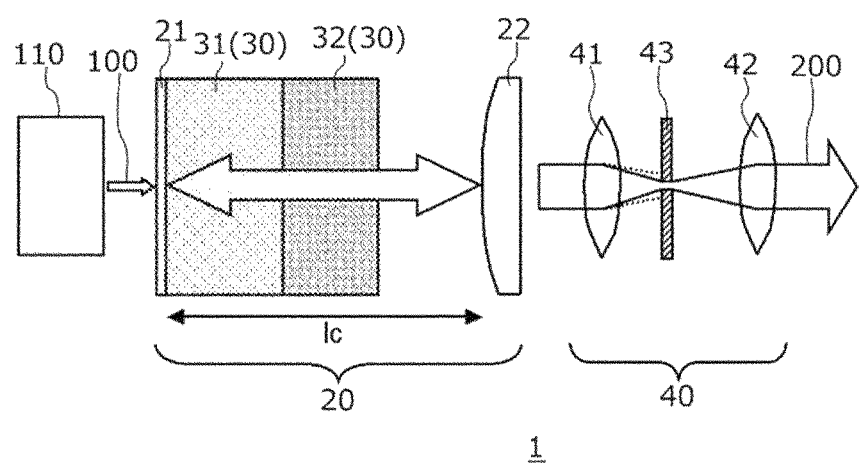
FIG. 1 illustrates a configuration of a laser device in accordance with an embodiment of the present invention.

The following description will discuss a laser device in accordance with Embodiment 1 of the present invention. Laser light generated by this laser device is especially preferably used as pump light for OPO that emits mid-infrared laser light. FIG. 1 illustrates a configuration of this laser device 1. It is assumed here that excitation light 100, which is laser light for use in oscillation in the laser device 1, and output light 200, which is laser light that is eventually outputted, share the same optical axis (horizontal direction in FIG. 1), and FIG. 1 illustrates a cross section extending along this optical axis.

The laser device 1 is arranged such that the excitation light 100, which is generated by the laser diode (excitation light source) 110, has a wavelength of 940±1.5 nm, which falls within the absorption wavelength range of Yb:YAG. An optical resonator 20 includes an incident mirror 21 and an exit mirror arranged such that the cavity length is $l_c$, and the excitation light 100 enters the optical resonator 20 via the incident mirror 21. The incident mirror 21 transmits the excitation light 100 but reflects the output light 200, whereas the exit mirror 22 is a half mirror; therefore, the optical resonator 20 is capable of (i) confining laser light that will eventually become the output light 200 between the incident mirror 21 and the exit mirror 22 and amplifying the light and (ii) receiving the excitation light 100 via the incident mirror 21 from left in FIG. 1 and outputting the output light 200 via the exit mirror 22 rightward in FIG. 1. The optical resonator 20 includes: a laser medium 31 that absorbs the excitation light 100 and thereby causes the light that will eventually become the output light 200 to oscillate; and a saturable absorber 32 that serves as a Q-switch, which are arranged along the optical axis. The pulse width of the laser light emitted by the laser diode 110, the cavity length $l_c$ of the optical resonator 20, and the saturable absorber 32 are set such that the laser light emitted by the laser diode 100 is single-pulsed laser light and that the output light 200 is composed of a plurality of pulses. A material constituting the laser medium 31 is Yb:YAG, which is obtained by doping yttrium-aluminum-garnet (YAG) with ytterbium (Yb), and therefore laser light (output light 200) that is caused to oscillate by stimulated emission in the laser medium 31 has a wavelength of about 1030 nm. A material constituting the saturable absorber 32 is Cr:YAG, which is obtained by doping YAG (which is the same as the base material for the laser medium 31) with chromium (Cr). This material has saturable properties (properties of absorbing low-intensity light and transmitting high-intensity light) with respect to the foregoing laser light.

In cases where the above laser device 1 is used in a blood glucose meter such as that disclosed in Patent Literature 1, the blood glucose meter as a whole, including the laser device serving as a source of pump light, is particularly required to be small in size. As is clear from the results of study by the inventors shown in FIG. 12, use of Yb:YAG provides a longer output pulse width $t_p$ while keeping the cavity length $l_c$ small. That is, use of Yb:YAG makes it possible to reduce the size of the source of pump light for OPO.

Note that the optical resonator 20 in accordance with Embodiment 1 actually employs a sintered optical element 30, which is an integrated, sintered body made up of the laser medium 31 and the saturable absorber 32. Furthermore, the incident mirror 21 is in the form of a thin film disposed on the surface of the sintered optical element 30 on the left side of FIG. 1 (on the laser medium 31-side surface of the sintered optical element 30). Specifically, the incident mirror 21 is a multilayer coating film that transmits light having a wavelength of 940 nm (excitation light 100) and reflects light having a wavelength of 1030 nm (output light 200). As such, actually, the incident mirror 21, the laser medium 31, and the saturable absorber 32 are integral with each other. In this case, the following arrangement can be employed: the entire sintered optical element 30, made up of the incident mirror 21, the laser medium 31, and the saturable absorber 32 which are integral with each other, is cooled by a laser medium cooler 80 constituted by a Peltier element and the like illustrated in FIG. 2 such that the temperature of the entire sintered optical element 30 is controlled. The laser medium cooler 80 is mainly composed of a highly thermally conductive metal such as copper, an aluminum alloy, or indium. The laser medium cooler 80 is constituted by: a holder 81 that heat-conductively holds a laser medium which is a heat source such as the sintered optical element 30; a top plate 82 that is in close contact with the holder 81; a thin heat exchanger plate 83; a Peltier element 84 (non-metal); a thin heat exchanger plate 85; a base plate 86; and a heat dissipator 87. The top plate 82 and the thin heat exchanger plate 83 are large in area, and transfer heat efficiently from the sintered optical element 30 to the top face of the Peltier element 84. The thin heat exchanger plate 85 is in close contact with the bottom face of the Peltier element 84, and efficiently dissipates heat to the base plate 86. With such an arrangement, the laser medium cooler 80 prevents or reduces temperature rise, of the laser medium, which would be caused by pump light's excitation energy that was not converted into laser light, and thereby contributes to stable oscillation in the laser device 1.

The heat dissipator 87, in cases of air cooling, is preferably in the form of a fin as illustrated in FIG. 2, and dissipates heat through forced circulation of air caused by a cooling fan or the like. This cooling feature makes it possible to control the temperatures of the saturable absorber 32 and the laser medium 31 to thereby control the longitudinal mode of the oscillating output light 200. Furthermore, in order to compensate for a reduction in mode size caused by a thermal lens effect resulting from the temperature rise of the laser medium 31, the exit mirror 22 is a convex mirror that is such that light reflected at the exit mirror 22 diverges within the optical resonator 20.

FIG. 3 shows the results of actual measurement of the relationship among the cavity length $l_c$, the output pulse width $t_p$ of the output light 200 which has been caused to oscillate, and pulse energy (per pulse), in this arrangement. An increase in cavity length $l_c$ results in increases in both the output pulse width and the pulse energy. As described earlier, when light from the resonator in accordance with Embodiment 1 is for use as pump light for OPO, the pulse width of the output light 200 is preferably long, for example, not less than 4 ns and not greater than 1 µs, preferably not less than 10 ns. For example, by employing a cavity length $l_c$ of 160 mm, it is possible to broaden the pulse width up to about 12 ns. The pulse energy in this case was 6.5 mJ, and the oscillation frequency of the output light 200 was about 60 Hz at the maximum.

Furthermore, in cases where the pulse width of the excitation light 100 is long and the duration of a continuous input of the excitation light 100 is long, the output light 200 is outputted a plurality of times during one continuous input of the excitation light 100. The Q-switching action of the saturable absorber 32 in such a case is such that, when excitation levels involved in light absorption are sufficiently occupied by electrons, light transmits and therefore the Q-switch turns on, and thereby the output light 200 is outputted.

If light absorption and light transmission are carried out in a similar manner immediately after that, since the excitation levels of the saturable absorber 32 are occupied to some extent, the Q-switch requires only a smaller amount of energy to turn on again, as compared to the energy required for the first output. FIG. 4 shows the pulse energy of the entire laser output per continuous input of excitation light, and efficiency, versus an increase in pulse width (equivalent to a change in excitation light energy) of a laser diode (LD) which is the excitation light, obtained under the conditions that the cavity length $l_c$ was 52.2 mm and that the output light 200 was outputted a plurality of times by carrying out light absorption and light transmission with respect to the saturable absorber immediately after the output of the previous pulsed light. This efficiency indicates the energy efficiency of the output light in relation to the excitation light energy. The numbers "1" to "4" in FIG. 4 each indicate the number of times the output light 200 is outputted in relation to the excitation light input, and correspond to one to four outputs.

For the reason as set forth above, subsequent pulses are easier to be outputted, have higher pulse energy, and have higher efficiency, and, in a case of four outputs, an efficiency of 10% is obtained. FIG. 5 shows the results of actual measurement of time course when the output light 200 is outputted four times as described above, and the pulse interval is about 60 to 80 µs. By using the output light 200 as pump light in generating laser light by OPO for a probe of a blood glucose meter disclosed in Patent Literature 1, it is possible to carry out the measurement a plurality of times per continuous input of laser diode excitation light, because measurements are carried out in correspondence with pulse repetitions. The above pulse interval is sufficiently shorter than the interval (10 ms [milliseconds] at the shortest) of the laser diode excitation light, but temporal separation of pulses with such intervals is still available in computation. As such, when pulsed light with such time interval is used, the output of the blood glucose meter is obtained per pulse of the light, and statistical processing of the output makes it possible to achieve highly accurate measurement. That is, such characteristics, in which the output light 200 is obtained in the form of a plurality of pulses, are preferred for measurements such as that disclosed in Patent Literature 1.

However, when the laser output light 200 that has been actually generated was used as pump light for OPO, the non-linear crystal in OPO was damaged even by low intensity. The cause of this is that, as a mode size within the optical resonator increased for the output pulse width $t_p$ to be longer, components other than a component $TEM_{00}$, which is the fundamental mode in the transverse oscillation mode, became large. That is, the transverse oscillation mode became likely to be multimodal, and, when such multimodal light entered the saturable absorber, the timing of the switching action of the saturable absorber became non-uniform, resulting in generation of components not functioning as pump light for OPO. Such useless components of the pump light do not contribute to the oscillation in OPO, and are absorbed by the non-linear crystal and cause heat generation. This may lead to damage to the non-linear crystal.

Also with a configuration in which the output pulse width $t_p$ of the foregoing output light 200 is long and in which the output light 200 is outputted in the form of a plurality of pulses during one continuous input of the excitation light 100, the mode size in the optical resonator 20 becomes large, and the transverse oscillation mode becomes multimodal (the modes other than the component $TEM_{00}$, which is fundamental mode, make greater contribution). Such situations, in which the transverse oscillation mode becomes multimodal, were especially noticeable when the output light 200 with a pulse width suitable for pump light for OPO, for example, a pulse width of not less than 10 ns, is to be obtained. In order to solve such an issue, it is demanded that, when a laser device is configured such that the output pulse width is long, the transverse oscillation mode be close to single mode.

To this end, the laser device 1 includes, as illustrated in FIG. 1, a spatial filter 40 situated in the optical path of the output light 200 which has been outputted from the optical resonator 20. The spatial filter 40 is a mechanism that filters out a portion of the output light 200 around the optical axis, and is constituted by a first lens 41, a second lens 42, and a diaphragm 43. The first lens 41 is an optical system that causes convergence of light, and is configured such that the output light 200 has a focus (beam waist) and converges at the position where the diaphragm 43 is present. The second lens 42 is provided downstream of the first lens 41, and is configured to collimate the output light 200. The diaphragm 43 is configured to allow only light at and near the optical axis, at the beam waist, to pass therethrough. This makes it possible to remove most of the components other than the component $TEM_{00}$ from the output light 200.

(a) of FIG. 6 is a cross-sectional view of the diaphragm 43 in accordance with Embodiment 1, and (b) of FIG. 6 is a front view of the diaphragm 43. As illustrated in (a) and (b) of FIG. 6, the diaphragm 43 is a flat member made of a ceramic material or the like, and includes: a path 431 that has an opening 431A; and a tapered portion 432. The path 431 of the diaphragm 43 is arranged such that the central axis thereof coincides with or substantially coincides with the optical axis of the output light 200.

The path 431 is a small hole that allows passage of only the light at and near the optical axis of the output light 200 at the beam waist of the output light 200. The opening 431A is in the form of preferably a perfect circle or a near-perfect circle. The diameter $d_a$ of the opening 431A is set with reference to the diffraction limit at the beam waist of the output light 200. Specifically, when the diameter $d_a$ of the opening 431A is slightly greater than the size of the diffraction limit at the beam waist, only the component $TEM_{00}$ can easily pass through the opening 431A.

The length $l_a$ of the path 431, for the purpose of allowing passage of only the component $TEM_{00}$, is preferably shorter than the length (Rayleigh length) of the beam waist. Note, however, that the length $l_a$ of the path 431 may be any length provided that it is not greater than 1.2 mm, in consideration of processing technique and the durability of the opening 431A.

The tapered portion 432 may be positioned upstream (closer to the laser diode 110) of the path 431 in the optical path of the output light 200 or may be positioned downstream (closer to the exit of the output light 200) of the path 431.

In cases where the tapered portion 432 is positioned upstream of the path 431, the diaphragm 43 is highly effective in filtering out or blocking light from the downstream side. On the other hand, in cases where the tapered portion 432 is positioned downstream of the path 431, the diaphragm 43 is highly effective in spatial filtering of light coming from the upstream side. The tapered portion 432 is a structure that is necessary to make the path 431 shorter than the Rayleigh length while keeping the mechanical strength of the diaphragm 43; however, light reflection at the tapered surface is not zero. Therefore, the tapered portion 432 is usually positioned on the opposite side of the path 431 from the source of light that is to be subjected to filtering (that is, positioned downstream of the path 431), in many cases.

Furthermore, the angle $\theta_a$ between the tapered portion 432 and the optical axis of laser light is preferably not less than 20° and less than 90°. If the angle is $\theta_a$ too small, long-distance light propagation is necessary for convergence of laser light associated with the spatial filtering, resulting in an increase in size of the device. This is not practical. Thus, the angle $\theta_a$ is preferably not less than 20°.

FIG. 7 shows the results of two-dimensional imaging, with the use of a CCD camera, of beam profiles (intensity distribution detected at a plane that is perpendicular to the optical axis) of the output light 200 in (a) a case where the spatial filter 40 was not used and (b) a case where the spatial filter 40 was used. In both cases, the cavity length $l_c$ was 137.2 mm. The highest intensity was obtained at the beam axis, and an intensity distribution spreading around the beam axis was obtained. In each of the images, the waveforms at the left and bottom of the image are one-dimensional beam profiles (normalized to the intensity at the optical axis) passing through the optical axis (axis of beam) along the vertical line and the horizontal line in FIG. 7, respectively. In this arrangement, the size of the opening of the diaphragm 43 was 1.2 times the diffraction limit size. In the case (a) where the spatial filter 40 was not used, the asymmetry about the optical axis was noticeable because the contribution of the components other than the component $TEM_{00}$ was unignorable; however, in the case where the spatial filter 40 was used, symmetry about the optical axis improved.

As described earlier, the output light 200 is emitted in a pulsed form. In this regard, the removal of the components other than the component $TEM_{00}$ results in a change in pulse shape of the output light 200. FIG. 8 shows the results of actual measurement of the pulse shape of output light corresponding to each case of FIG. 7. Note here that the vertical axis in FIG. 8 shows normalized intensity obtained through normalization by dividing the entire intensity by the maximum value of each pulse. The intensity is normalized such that the maximum value of each pulse is 1. The FWHM value of the pulse was 11.4 ns when the spatial filter 40 was not used, and was shorter (10.8 ns) when the spatial filter 40 was used. That is, since the components other than the component $TEM_{00}$ have broader pulse width than the component $TEM_{00}$, the removal of the components other than the component $TEM_{00}$ makes the pulse width slightly shorter. In FIG. 8, when the spatial filter 40 is provided, the energy is partially lost because of the spatial filter 40. The energy lost is 23.7% of that in the case where the spatial filter 40 is absent. The FWHM of the pulse corresponding to the blocked components is 13.6 ns.

In cases where mid-infrared laser light is caused to stably oscillate, there is a threshold for the intensity of pump light. In cases where mid-infrared laser light is caused to oscillate by OPO, pump light with an intensity equal to or greater than the threshold is required. In cases where the output light 200 that has been generated in the same conditions as shown in FIG. 7 was actually used as pump light for OPO, the threshold in the case where the spatial filter 40 was absent was about 3.7 $MW/cm^2$, whereas the threshold decreased to about 2.3 $MW/cm^2$ when the spatial filter 40 was provided. That is, when the mid-infrared laser light is caused to stably oscillate by OPO, since useless components are removed from the pump light by the spatial filter 40, the threshold can be lowered by about 40%, which exceeds the loss effect at the spatial filter. This reduces the damage to the non-linear crystal of OPO.

As the opening size of the diaphragm 43 decreases, the diaphragm 43 becomes more effective as the spatial filter; however, also a greater proportion of the component $TEM_{00}$ is blocked at this opening and the intensity of the output light 200 decreases. Therefore, the size of the opening is preferably slightly greater than the diffraction limit size at the beam waist, particularly preferably about 1.0 to 1.4 times the diffraction limit size. Although the spatial filter 40 employed here is arranged such that there is an optical system (first lens 41, second lens 42) which forms a beam waist in the optical path and that the diaphragm 43 is situated at the beam waist, the configuration of the spatial filter 40 may be any configuration, provided that similar effects are obtained. As used herein, the term "diffraction limit size" is intended to mean the diameter of laser light at the beam waist formed by the spatial filter, and the "opening size" of the diaphragm 43 is intended to mean the diameter $d_a$ of the opening in the diaphragm 43.

In the structure illustrated in FIG. 1, the optical resonator 20 includes the sintered optical element 30, which is constituted by the incident mirror 21, the laser medium 31, and the saturable absorber 32 which are integral with each other. Note however that, like a laser device 2 (Variation 1) illustrated in FIG. 9, an optical resonator 50 may include an incident mirror 25, a laser medium 26, and a saturable absorber 27 which are provided separately. In this case, the shape and material of the incident mirror 25 and the saturable absorber 27 can be selected irrespective of the laser medium 26; therefore, optimization of the optical resonator 50 is especially easy.

The wavelength at which oscillation occurs depends on the type of laser medium, and a material constituting the saturable absorber is selected in consideration of the type of laser medium and the characteristics of laser light to be caused to oscillate. In the foregoing laser device 1, Cr:YAG is used as the saturable absorber 32; however, some other material can alternatively be used as the saturable absorber. Generally, an optical material doped with Cr (such as Cr:ZnSe) can be used as a material for such a saturable absorber. In cases where the saturable absorber 27 and the laser medium 26 are provided separately as illustrated in FIG. 9, the degree of freedom in such material selection is high.

Furthermore, in the arrangement of FIG. 1, the spatial filter 40 is positioned outside (downstream) of the optical resonator 20; however, the spatial filter can be positioned within the optical resonator. FIG. 10 illustrates a configuration of a laser device 3 (Variation 2) having such an arrangement. An optical resonator 70 in FIG. 10 is configured such that: a beam waist is formed at a position within the optical resonator 70 other than the positions of a laser medium 31 and a saturable absorber 32 because of a lens effect resulting from the radii of curvature of an incident mirror 21 and an exit mirror 22 and heat generation in the laser medium 31; and a diaphragm 61, which serves as a spatial filter 60, is provided at the position of the beam waist. The diaphragm 61 has the same functions as the foregoing diaphragm 43.

As described earlier, when light from the optical resonator shown in FIG. 1 is for use as pump light in OPO for oscillation of mid-infrared light, a laser device needs to be configured such that the cavity length $l_c$ is long. In the arrangement of FIG. 1, it is necessary that the spatial filter 40 be further provided outside the long optical resonator 20. In contrast, in the arrangement of FIG. 10, the spatial filter 60 is provided only within the long optical resonator 70, and no spatial filter is necessary outside the optical resonator 70. This makes it possible to reduce the length and size of the entire arrangement. Especially in cases where the sintered optical element 30 made up of the incident mirror 21, the laser medium 31 and the saturable absorber 32 which are integral with each other is used as described earlier, the structure containing all these members therein can be reduced in size, because these members are united. On the other hand, the cavity length $l_c$ is long, and therefore the optical resonator 70 can save a large space for the spatial filter 60. As such, in the case where a laser medium and a saturable absorber which are integral with each other are used, it is particularly preferable that the spatial filter is provided inside the optical resonator.

In the above examples, Yb:YAG is used as the laser medium and Cr:YAG or Cr:ZnSe is used as the saturable absorber. Note, however, that in cases where the cavity length is long similarly to the above arrangement, providing the spatial filter like that described above is also effective even in cases where some other laser medium and saturable absorber are used. Furthermore, the output light from this laser device is used in OPO in the above examples; however, also for use for some other purpose, the earlier-described arrangement is also effective, if the pulse width of the output light is preferably broad and the transverse oscillation mode is preferably made monomodal.

Embodiment 2

FIG. 11 illustrates a configuration of a measurement apparatus 300 in accordance with Embodiment 2. The measurement apparatus 300 carries out measurement of a substance contained in a to-be-measured object 320 by irradiating the to-be-measured object 320 with wavelength-converted light 201 and measuring the absorbance of reflected light 201A reflected at the to-be-measured object 320. The to-be-measured object 320 is, for example, a living body (particularly human body), but is not limited to a particular kind. The substance is, for example, sugar in the blood, but is not particularly limited. The measurement apparatus 300 may be a blood glucose meter or may be some other apparatus for determining the quantity of substance in a living body non-invasively (for example, pulse oximeter).

As illustrated in FIG. 11, the measurement apparatus 300 includes a light source 310 and a light detector 330. The light source 310 includes a laser device 1, an optical parametric oscillator (OPO) 311, and an optical system 315. The laser device 1 is identical to the laser device 1 in accordance with Embodiment 1.

The OPO 311 is a device that includes a non-linear crystal which wavelength-converts laser light coming from the laser device 1, and includes an incident side half mirror 312, an exit side half mirror 314, and a non-linear crystal 313 disposed between the incident side half mirror 312 and the exit side half mirror 314. Output light 200 that passes through the incident side half mirror 312 enters on the non-linear crystal 313, and is converted to light having a wavelength longer than that of the output light 200, and when the light is reflected and confined between the incident side half mirror 312 and exit side half mirror 314, the light is amplified by optically parametric amplification. The amplified light passes through the exit side half mirror 314, becomes wavelength-converted light 201 and is outputted.

As the non-linear crystal 313, AgGaS that is suitable for this kind of wavelength conversion is used under the condition of phase matching. By adjusting the type and matching conditions of the non-linear crystal 313, it is possible to adjust the wavelength (oscillation wavelength) of the emitted wavelength-converted light 201. As the non-linear crystal, it is also possible to use GaSe, $ZnGeP_2$, $CdSiP_2$, $LiInS_2$, $LiGaSe_2$, $LiInSe_2$, $LiGaTe_2$ and the like. The wavelength-converted light 201 that is emitted from the OPO 311 has a repetition frequency and a pulse width that correspond to the output light 200.

The optical system 315 is a member that outputs the light that has been wavelength-converted by the OPO 311. The optical system 315 may include a condenser lens and/or a beam splitter. For example, by including a condenser lens as the optical system 315, it is possible to reduce the beam spot size.

The light detector 330 receives the reflected light 201A from the to-be-measured object 320, and outputs the intensity of the reflected light 201A as an electrical signal.

Note that, although Embodiment 2 deals with an example in which light reflected at the to-be-measured object 320 is detected by the light detector 330, the measurement apparatus may alternatively be arranged such that light that has passed through the to-be-measured object 320 is detected by the light detector 330.

REFERENCE SIGNS LIST 1, 2, 3 laser device
20, 50, 70 optical resonator
21, 25 incident mirror
22 exit mirror
26, 31 laser medium
27, 32 saturable absorber
30 sintered optical element
40, 60 spatial filter
41 first lens
42 second lens
43, 61 diaphragm
431 path
431A opening
432 tapered portion
80 laser medium cooler
81 holder 82 top plate
83, 85 thin heat exchanger plate
84 Peltier element
86 base plate
87 heat dissipator
100 excitation light
110 laser diode (excitation light source)
200 output light
300 measurement apparatus
310 light source
311 optical parametric oscillator (OPO)
313 non-linear crystal
315 optical system
330 detector

The invention claimed is:

1. A light source comprising:
a laser device configured to generate pulsed laser light by passive Q-switching;
an optical parametric oscillator, wherein the optical parametric oscillator comprises a non-linear crystal which is configured to wavelength-convert laser light outputted by the laser device, and
an optical system configured to output the laser light which has been wavelength-converted by the optical parametric oscillator;
wherein the laser device comprising further comprises an optical resonator that includes a saturable absorber and a laser medium that is arranged to emit light upon absorption of excitation light, the laser medium being arranged to emit the light upon an input of the excitation light, which is pulsed light, into the optical resonator, the optical resonator being arranged to amplify the light emitted by the laser medium to obtain laser light and output the laser light as output light,
the laser medium being doped with ytterbium (Yb),
a pulse width of the excitation light, a cavity length of the optical resonator, and the saturable absorber being set such that the excitation light is single-pulsed light and that the output light is composed of a plurality of pulses,
the cavity length of the optical resonator being equal to or more than 50 mm,
the laser device further comprising a spatial filter for controlling temporal waveform, the spatial filter being disposed in an optical path of the light inside the optical resonator or disposed in an optical path of the output light outside the optical resonator, the spatial filter being configured to filter out a portion of the light or of the output light around an optical axis so as to bring a transverse oscillation mode close to single mode,
wherein the laser device is for use as a source of pump light for optical parametric oscillation and the spatial filter is able to eliminate, from originally generated light, light components which do not contribute to optical parametric oscillation, and
wherein the laser light that enters the non-linear crystal has an intensity of not less than 2.3 MW/cm$^2$ and not more than 10 MW/cm$^2$.

2. The light source laser device according to claim 1, wherein the laser medium is a medium obtained by doping yttrium-aluminum-garnet (YAG) with ytterbium (Yb).

3. The light source laser device according to claim 1, wherein an output pulse width of the output light is not less than 4 ns.

4. The light source laser device according to claim 2, wherein an output pulse width of the output light is not less than 4 ns.

5. The light source laser device according to claim 1, wherein the spatial filter includes: an optical system that is configured to cause light to converge; and a diaphragm that is configured to filter out a portion of the light around the optical axis at a beam waist of the light.

6. The light source laser device according to claim 1, wherein the saturable absorber is doped with chromium (Cr).

7. The light source laser device according to claim 6, wherein the saturable absorber is a saturable absorber obtained by doping yttrium-aluminum-garnet (YAG) with chromium (Cr).

8. The light source laser device according to claim 7, wherein the laser medium and the saturable absorber are integral with each other.

9. The light source laser device according to claim 1, wherein the spatial filter has a light path extending therethrough, the light path comprising a cylindrical opening portion, a diameter of the opening portion is 1.0 to 1.4 times a diffraction limit size at a beam waist of the light.

10. A measurement apparatus comprising:
a light source as set forth in claim 1; and
a light detector that is configured to detect light that has been outputted by the light source and reflected at a to-be-measured object or that is configured to detect light that has been outputted by the light source and passed through the to-be-measured object.

11. The light source laser device according to claim 1, wherein the laser device is used for pumping, in an optical parametric oscillation, OPO, scheme a mid-infrared laser for measurement of a substance contained in a living body.

12. The light source laser device according to claim 1, wherein the spatial filter is disposed in an optical path of the light inside the optical resonator.

13. A light source comprising:
a laser device that generates pulsed laser light by passive Q-switching;
an optical parametric oscillator, wherein the optical parametric oscillator comprises a non-linear crystal which is configured to wavelength-convert laser light outputted by the laser device, and
an optical system that is configured to output the laser light which has been wavelength-converted by the optical parametric oscillator;
the laser device comprising an optical resonator that includes a saturable absorber and a laser medium that is arranged to emit light upon absorption of excitation light, the laser medium being arranged to emit the light upon an input of the excitation light, which is pulsed light, into the optical resonator, the optical resonator being arranged to amplify the light emitted by the laser medium to obtain laser light and output the laser light as output light,
the laser medium being doped with ytterbium (Yb),
a pulse width of the excitation light, a cavity length of the optical resonator, and the saturable absorber being set such that the excitation light is single-pulsed light and that the output light is composed of a plurality of pulses,
the laser device comprising a spatial filter that is disposed in an optical path of the light inside the optical resonator or that is disposed in an optical path of the output light outside the optical resonator, the spatial filter:
having a light path extending therethrough, the light path comprising (i) a cylindrical opening portion and (ii) a tapered portion adjacent to the cylindrical opening portion, each of the cylindrical opening portion and the tapered portion being configured such that the light or the output light extends therethrough, and being configured to filter out a portion of the light or of the output light around an optical axis so as to bring a transverse oscillation mode close to single mode, wherein the spatial filter is disposed at a beam waist of the light;

wherein the laser device is for use as a source of pump light for optical parametric oscillation, and the spatial filter is able to eliminate, from originally generated light, light components which do not contribute to optical parametric oscillation, and wherein the laser light that enters the non-linear crystal has an intensity of not less than 2.3 MW/cm$^2$ and not more than 10 MW/cm$^2$.

14. The light source laser device according to claim 13, wherein the laser device is used for pumping, in an optical parametric oscillation, OPO, scheme a mid-infrared laser for measurement of a substance contained in a living body.

15. A method for using a light source comprising a laser device that generates pulsed laser light by passive Q-switching, an optical parametric oscillator, wherein the optical parametric oscillator comprises a non-linear crystal which is configured to wavelength-convert laser light outputted by the laser device, and an optical system that is configured to output the laser light which has been wavelength-converted by the optical parametric oscillator, the laser device comprising an optical resonator that includes a saturable absorber and a laser medium that is arranged to emit light upon absorption of excitation light, the laser medium being arranged to emit the light upon an input of the excitation light, which is pulsed light, into the optical resonator, the optical resonator being arranged to amplify the light emitted by the laser medium to obtain laser light and output the laser light as output light, the laser medium being doped with ytterbium (Yb), a pulse width of the excitation light, a cavity length of the optical resonator, and the saturable absorber being set such that the excitation light is single-pulsed light and that the output light is composed of a plurality of pulses, the cavity length of the optical resonator being equal to or more than 50 mm, the laser device further comprising a spatial filter for controlling temporal waveform, the spatial filter being disposed in an optical path of the light inside the optical resonator or disposed in an optical path of the output light outside the optical resonator, the spatial filter being configured to filter out a portion of the light or of the output light around an optical axis so as to bring a transverse oscillation mode close to single mode, the method comprising:

emitting the laser light from the laser device to an optical parametric oscillator which includes a non-linear crystal; and wavelength-converting, by the optical parametric oscillator, the emitted laser light to light with a wavelength longer than that of the laser light;

wherein the laser device is for use as a source of pump light for optical parametric oscillation, and the spatial filter is able to eliminate, from originally generated light, light components which do not contribute to optical parametric oscillation, and wherein the laser light that enters the non-linear crystal has an intensity of not less than 2.3 MW/cm$^2$ and not more than 10 MW/cm$^2$.

16. The method according to claim 15, wherein the spatial filter has a light path extending therethrough, the light path comprising a cylindrical opening portion, a diameter of the opening portion is 1.0 to 1.4 times a diffraction limit size at a beam waist of the light.

* * * * *